(12) United States Patent
Kamiya et al.

(10) Patent No.: US 7,713,545 B2
(45) Date of Patent: May 11, 2010

(54) N-GLYCOSIDE TYPE GLYCOLIPIDS AND HOLLOW FIBER TYPE ORGANIC NANOTUBES MADE OF THE SAME

(75) Inventors: Shoko Kamiya, Ibaraki (JP); Toshimi Shimizu, Ibaraki (JP); Jong Hwa Jung, Daejeon (KR)

(73) Assignees: Japan Science and Technology Agency, Saitama (JP); National Institute of Advanced Industrial Science and Technology, Tokyo (JP)

( * ) Notice: Subject to any disclaimer, the term of this patent is extended or adjusted under 35 U.S.C. 154(b) by 808 days.

(21) Appl. No.: 10/543,865

(22) PCT Filed: Dec. 25, 2003

(86) PCT No.: PCT/JP03/16830
§ 371 (c)(1),
(2), (4) Date: Jul. 26, 2005

(87) PCT Pub. No.: WO2004/065399
PCT Pub. Date: Aug. 5, 2004

(65) Prior Publication Data
US 2006/0160248 A1 Jul. 20, 2006

(30) Foreign Application Priority Data
Jan. 22, 2003 (JP) .............................. 2003-013266

(51) Int. Cl.
*A61K 9/127* (2006.01)
*C07H 5/06* (2006.01)

(52) U.S. Cl. ........................ 424/450; 977/706; 977/742

(58) Field of Classification Search ................. 424/450; 977/706, 742
See application file for complete search history.

(56) References Cited

U.S. PATENT DOCUMENTS

| 4,683,222 A | 7/1987 | Stadler et al. |
| 4,983,725 A | 1/1991 | Miyaji et al. |
| 5,567,413 A | 10/1996 | Klaveness et al. |
| 5,910,490 A | 6/1999 | Moczar et al. |
| 6,897,326 B2 | 5/2005 | Masuda et al. |

FOREIGN PATENT DOCUMENTS

| EP | 1186688 | 3/2002 |
| JP | 62-209092 | 9/1987 |
| JP | 11-255791 | 9/1999 |
| WO | WO 02/090370 | 11/2002 |

OTHER PUBLICATIONS

Kim, J.-S., Pak, Y.K., Chun, K.H. and Shin, J.E.N. (2001) Preparation of N-Acryloyl and N-(N-Acryloylglycinyl) Derivatives of 2-Acetoamido-2-deoxy-β-D-glucopyranosylamine. Bulletin of the Korean Chemical Society, vol. 22, No. 7, p. 758-760.*
Gronwalk, O., Sakurai, K., Luboradzki, R., Kimura, T., Shinkai, S. (2001) Further evidence for the gelation ability-structure correlation in sugar based gelators. Carbohydrate Research, vol. 331, p. 307-318.*
Masuda et al., Polymerization of Bolaform Butadiyne 1-Glucosamide . . . :, Macromolecules 1998, 9403-9405.
U.S. Appl. No. 10/497,090, filed May 28, 2004.
U.S. Appl. No. 10/507,576, filed Sep. 10, 2004.
U.S. Appl. No. 10/544,800, filed Aug. 4, 2005.
Yang et al., "Effective Shortening in Length of Glycolipid Nanotubes with High Axial Ratios", Chem. Letters 32, 1146-1147 (2003).

* cited by examiner

*Primary Examiner*—Shaojia Anna Jiang
*Assistant Examiner*—Scarlett Goon
(74) *Attorney, Agent, or Firm*—Gary C Cohn PLLC

(57) ABSTRACT

Presents novel hollow fiber shaped organic nanotubes that can be easily produced in a short time span and also have a broad range of utility. An N-glycoside type glycolipid represented by the general formula (1) shown below.

$$G-NHCO-R \qquad (1)$$

(In the formula, G represents a saccharide radical other than a hemiacetal hydroxyl group bonded to the anomer carbon atom of the saccharide, and R represents an unsaturated hydrocarbon group containing ten to 39 carbon atoms.) This molecule self-aggregates and forms hollow fiber shaped organic nanotubes in water when this N-glycoside type glycolipid is dissolved, allowed to cool gradually and allowed to stand undisturbed at room temperature. The average external diameter of the nanotubes is from 70 nm to 500 nm and the average internal diameter (average diameter of the cavity) is from 40 nm to 300 nm.

3 Claims, 2 Drawing Sheets

N-GLYCOSIDE TYPE GLYCOLIPIDS AND HOLLOW FIBER TYPE ORGANIC NANOTUBES MADE OF THE SAME

TECHNICAL FIELD

The present invention relates to a novel N-glycoside type glycolipid, organic nanotubes thereof and a production process thereof.

PRIOR ART

Glycolipids wherein long chain saturated type hydrocarbon chains are bonded to the carbon atom (an asymmetric carbon in position 1) in the anomer position in a saccharide group through an amide linkage (Tetrahedron Letters, Vol. 32, No. 12, pp. 1557-1560 (1991); Carbohydrate Research, 324 (2000) 97-106)) and glycolipids wherein long chain unsaturated type hydrocarbon chains are bonded to the carbon atom in position 2 of the saccharide group through an amide bond (Chemical Abstracts, Vol. 126, No. 14, page 754 (1997)) are known.

In addition, glycolipids wherein aldose groups and unsaturated linear hydrocarbons containing an aromatic ring are bonded (Unexamined Japanese Patent Application 2000-271192) and glycolipids wherein a saturated linear carboxylic acid is bonded to an aldopyranose group through an amide linkage (Unexamined Japanese Patent Application 2002-322190) are known to form hollow nanotube shaped coagulates by the hydrogen bond of saccharide when being heated and dispersed in water and cooled gradually.

Although fiber like molecular aggregates are known to form when glycolipids bonded with long chain unsaturated alkyl chains through an amide linkage to the carbon atom in position 2 of the saccharide group are allowed to self accumulate in water, the shape of the fiber comprising these glycolipids bonded with long chain unsaturated alkyl chains through an amide linkage to the carbon atom in position 2 of the saccharide group is not a hollow tube (Tsujimoto et al. "Synthesis and Enzyme Hardening of Microfibers Utilizing Vegetable Oils and Fats" "Polymer Society Annual Meeting Abstract" Vol. 51, page 305 (Polymer Reprints, Japan, Vol. 51, No. 2 (2002))

Problems for the Invention to Solve

The objective of the present invention is to provide a novel hollow fiber shaped organic nanotube that can be easily produced in a short duration of time and yet has a broad utility range.

Means to Solve the Problems

The inventors conducted investigations of the linkage positions of a hydrocarbon chain that is an aglycon and a saccharide in order to solve the above mentioned problem. As a result, the inventors discovered that hollow fiber shaped organic nanotubes can be obtained by preparing a novel N-glycoside type glycolipid using an unsaturated hydrocarbon group as the aglycon and bonding it to the anomer carbon atom (position 1) of the saccharide through an amide linkage and allowing this glycolipid to undergo pseudo crystallization upon molecular aggregation. The present invention was completed based on this discovery.

That is, the present invention is an N-glycoside type glycolipid represented by the general formula (1) shown below.

G-NHCO—R         (1)

(In the formula, G represents a saccharide radical from which the hemiacetal hydroxyl group bonded to the anomer carbon atom of the saccharide is excluded, and R represents an unsaturated hydrocarbon group containing 10-39 carbon atoms.).

In addition, the present invention is a hollow fiber shaped organic nanotube comprising this N-glycoside type glycolipid as the constitutional component.

Furthermore, the present invention is a production method for the hollow fiber shaped organic nanotubes comprising the steps of dissolving the N-glycoside type glycolipid as in any one of claims 1-3 in a hot solvent at its boiling point or lower, cooling gradually the solution formed and allowing the solution to stand undisturbed at room temperature.

DETAILED DESCRIPTION OF THE INVENTION

Figure 1:
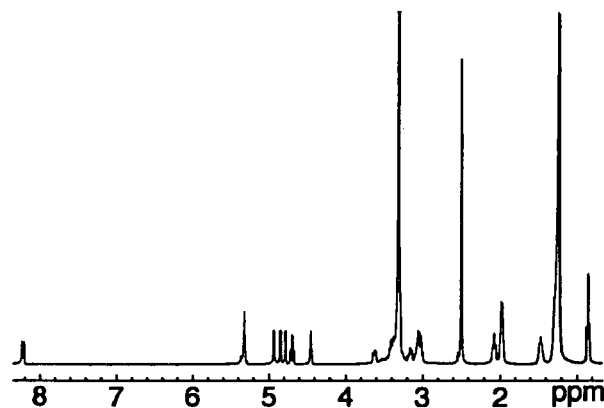
FIG. 1 shows a $^1$H-NMR spectrum of the N-glycoside type glycolipid [N-(11-cis-octadecenoyl)-β-D-glucopyranosylamine] prepared in Example 1.

The N-glycoside type glycolipid of the present invention is an N-glycoside type glycolipid containing an unsaturated hydrocarbon group as the aglycon, that is, an N-glycoside type glycolipid represented by the general formula (1) G-NHCO—R, and this glycolipid can be used as a starting material to manufacture hollow fiber type organic nanotubes and micro tubes.

In the general formula (1), G is a saccharide radical from which the hemiacetal hydroxyl group bonded to the anomer carbon atom of a saccharide is excluded, and glucopyranose, galactopyranose, maltose, lactose, cellobiose and ketobiose may be cited as the saccharide with glucopyranose being preferred. This saccharide may be a monosaccharide or an oligosaccharide, but a monosaccharide is preferred. This saccharide radical may be any one of D, L or racemic materials, but naturally derived saccharide radicals are ordinarily a D type. Furthermore, the anomer carbon atom is an asymmetric carbon atom in an aldopyranosyl group, and an a-anomer and a β-anomer exist. However, any one of an α-anomer or a β-anomer or a mixture thereof may be used. Having G be a D-glucopyranosyl group or a D-galactopyranosyl group is ideal from the standpoint of raw material availability and ease of manufacturing, but G being a D-glucopyranosyl group is particularly ideal.

R in the above mentioned general formula (1) is an unsaturated hydrocarbon group, preferably a linear group, and the presence of three or fewer double bonds as the unsaturated bond is further preferred. In addition, the number of carbon atoms present in R is 10 to 39, but 15 to 20 is preferred and 17 is more preferred. The undecyl group, the dodecyl group, the tridecyl group, the tetradecyl group, the pentadecyl group, the hexadecyl group, the heptadecyl group, the octadecyl group, the nonadecyl group, the eicosyl group, the heneicosyl group, the docosyl group, the tricosyl group, the tetracosyl group, the pentacosyl group, the hexacosyl group, the heptacosyl group, the octacosyl group and the like containing monoene, diene, triene and the like segments as the unsaturated bonds may be cited as this type of hydrocarbon group.

The production method used to produce the N-glycoside type glycolipids of the present invention is not particularly restricted. However, this N-glycoside type glycolipid can be produced, for example, by forming an N-glycoside bond by allowing an unsaturated type long chain carboxylic acid represented by the general formula, R—COOH [R in the formula has the same significance as the R in the general formula (1)], or an unsaturated type long chain carboxylic acid chloride represented by the general formula, R—COCl [R in the formula has the same significance as the R in the general formula (1)], to react with a saccharide amine containing an amino group in the anomer position.

The production method for this saccharide amine is not particularly restricted, but this saccharide amine can be produced, for example, as follows.

A specific saccharide (aldopyranose or its oligosaccharide) and ammonium hydrogen carbonate are dissolved in water. The aqueous solution temperature is preferably 37° C. As a result, this ammonium hydrogen carbonate selectively reacts with the hemiacetal hydroxyl group bonded to the anomer carbon atom of the saccharide and yields an amino compound containing an amino group on the anomer carbon atom (position 1) of the saccharide, a so-called aminosaccharide. In this reaction, a β isomer is selectively obtained.

10-Undecenoic acid, 11-dodecenoic acid, 12-tridecenoic acid, 9-tetradecenoic acid, 10-pentadecenoic acid, 9-hexadecenoic acid, 10-heptadecenoic acid, 6-octadecenoic acid, 9-octadecenoic acid, 11-octadecenoic acid, 9-12 octadecadienoic acid, 6-9-12 octadecatrienoic acid, 9-12-15 octadecatrienoic acid, 7-nonadecenoic acid, 10-nonadecenoic acid, 10-13 nonadecadienoic acid, 5-eicosenoic acid, 8-eicosenoic acid, 11-eicosenoic acid, 11-14 eicosadienoic acid, 8-11-14 eicosatrienoic acid, 11-14-17 eicosatrienoic acid, heneicosanoic acid, 13-docosenoic acid, 13-16 docosadienoic acid,13-16-19 docosatrienoic acid, 14-tricosenoic acid, 15-tetracosenoic acid, 10-12 tricosadienoic acid, 10-12 pentacosadienoic acid, 10-12 heptacosadienoic acid, 10-12 nonacosadienoic acid and the like may be cited as the unsaturated type long chain carboxylic acid. Of these, 11-octadecenoic acid is desirable based on the well balanced amphiphilic property of the glycolipid and the melting point in water.

A condensation agent may be used as a reaction accelerating agent for the reaction of an unsaturated type long chain carboxylic acid and a glycoamine. As this condensation agent, benzotriazol-1-yl-oxy-tris(dimethylamino 0-phosphonium hexafluoro phosphate (henceforth referred to as "BOP"), 1-hydroxybenzotriazole (henceforth referred to as "HOBt", benzotriazole-1-yl-oxy-tripyrrolidino phosphonium hexafluorophosphate (henceforth referred to as "PyBOP"), O—(benzotriazol-1-yl)-N,N,N',N'-tetramethyluronium hexafluoro phosphate (henceforth referred to as "HBTU"), diphenyl(2,3-dihydro-2-thioxo-3-benzoxazolyl) phosphonate (henceforth referred to as "DBP") and the like may be cited. Of these, a combination of BOP and HOBt is preferred due to a high yield reaction.

A reaction to form an N-glycoside bond from the above mentioned glycoamine and the unsaturated type long chain carboxylic acid can be conducted, for example, as described below.

HOBt and BOP are used as condensation agents and dimethyl sulfoxide is used as the solvent. They are agitated using a magnetic stirrer at room temperature for at least five hours. The molar ratio for the components, a fatty acid:glycoamine: HOBt: BOP=1:1-100:1-100:1-100, is preferred, and 1:2 or more:1:3 is particularly preferred. That is, a glycoamine and a condensation agent are added in excess to a fatty acid.

The scope of the binding agent other than the combination of HOB and BOP includes the use of DBP alone, a combination of HOB and HBTU, a combination of HOBt and PYBOP, a combination of DBP and triethylamine (TEA) and a combination of HOBt, HBTU and N,N-diisopropyl ethylamine (DIEA).

In order to activate the carboxylic acid of a fatty acid prior to a reaction, the addition of a glycoamine is desired after the fatty acid and a condensation agent are first mixed in a solvent for about ten minutes. Upon completion of the reaction, the crude product is purified to obtain a high purity product using a separation and purification operation using a silica gel column and Toro Pearl HW-40S.

On the other hand, oleoyl chloride, cis-vaccenoyl chloride and linoleoyl chloride may be cited as the unsaturated type long chain carboxylic acid chloride.

The reaction used to form an N-glycoside bond from the above mentioned glycoamine and the unsaturated type long chain carboxylic acid chloride may be, for example, conducted as described below. A reaction mixture is agitated using a magnetic stirrer for at least five hours at a reaction temperature of 0° C. in the presence of a basic substance. Methanol, water, tetrahydrofuran and the like may be cited as the solvent. In order to activate the amino group of the glycoamine prior to the reaction, the addition of an unsaturated long chain carboxylic acid chloride is desirable after mixing a glycoamine and a basic substance in a solvent at 0° C. for about two hours first.

As a result of the reaction described above, an N-glycoside type glycolipid of the present invention in which an unsaturated hydrocarbon group is bonded to the anomer carbon atom (position 1) of a saccharide through an amide linkage is formed. The structure of the N-glycoside type glycolipid formed can be confirmed using an $^1$H-NMR spectrum or a $^{13}$C-NMR spectrum.

Next, a hollow fiber shaped organic nanotube production method using an N-glycoside type glycolipid synthesized in the manner described above is described.

First, a solvent such as water is added to the N-glycoside starting material and heated to prepare a solution. A higher concentration of the N-glycoside in this solution is preferred, and a saturated solution is most preferred.

Water is ordinarily used alone as the solvent used to prepare this aqueous solution. However, a mixed solvent of water and an organic solvent may also be used. Hydrophilic solvents such as dimethyl sulfoxide, acetone, methyl alcohol, ethyl alcohol, propyl alcohol and the like may be cited as the organic solvent.

When the amount of the solvent in the solution is too low at this point, an insoluble fraction remains. When too much solvent is used, the saturation concentration is not achieved. Therefore, the amount of the solvent added is selected from within a range of from 10,000 to 40,000 fold by weight.

A heating temperature as high as possible is preferred for this step in order to increase the amount of N-glycoside dissolved. Raising the temperature to the boiling point of the solution is preferred, but a temperature lower than that level may also be used. This temperature is more specifically from 80° C. to the boiling point, but from 90° C. to the boiling point is preferred and the boiling point is most preferred.

An N-glycoside solution prepared in the manner described above is allowed to cool gradually and allowed to stand still at room temperature to form hollow fiber shaped organic nanotubes. Here the term "cool gradually" has two meanings. One meaning is that a temperature is allowed to fall without conducting a specific heating and cooling operation. The other meaning is that the temperature is allowed to fall slowly while controlling the temperature by conducting a heating or cooling operation. Therefore, the temperature during the gradual cooling in one case may vary according to the temperature of the surroundings and the heat capacity of the device used in one case while the temperature in the other case may depend on the setting of a device that controls the temperature. In addition, the term "room temperature" means that a temperature is not subjected to particularly excessive heating or cooling, and the room temperature specifically refers to from 0° C. to 40° C. or preferably a temperature in the vicinity of 20° C. A fibrous substance separates from the solution after the solution is gradually cooled for from a little over ten hours to several days.

This fibrous substance is collected and air dried or vacuum dried to yield air stable hollow fiber shaped organic nanotubes having an average external diameter of from 70 nm to 500 nm, preferably from 200 nm to 500 nm, having an average internal diameter (average diameter of the cavity) of from 40 nm to 300 nm or preferably from 50 nm to 300 nm and having a length of from several hundred nm to several hundred μm.

The shapes of the hollow fiber shaped organic nanotubes obtained can be readily observed using an ordinary optical microscope. The tubular construction can be confirmed with further detail by using a laser, atomic power or electron microscope.

EFFECT OF THE INVENTION

The hollow fiber shaped organic nanotubes of the present invention can be utilized in, for example, fine chemical industries, the pharmaceutical field, the cosmetic field and the like as a packaging and separating material for pharmaceutical drugs and useful biomolecules and as a drug delivery material. In addition, the nanotubes may be coated with an electroconductive substance or a metal and used as micro electronic parts in the electronic and data fields. Furthermore, the nanotubes are useful as a gas storing material in the energy industry, are useful in man-made blood vessels, nanotube capillaries and nano reactors that utilize the micro tubular structure in the medical, analytical and chemical production fields and have excellent industrial utility value.

The present invention is illustrated by the examples below, but these examples are not intended to restrict the present invention.

SYNTHETIC EXAMPLE 1

D-(+)-glucopyranose (1.0 g, 5.55 millimoles, manufactured by the Fluka Co.) was placed in a flask, and 50 ml of water was added to dissolve it. Ten grams of ammonium hydrogen carbonate (manufactured by the Wako Co.) was added until crystals separated out in the bottom of the flask. The mixture was agitated using a magnetic stirrer for three to five days at 37° C. in an oil bath. Ammonium hydrogen carbonate was added from time to time to maintain the reaction in a saturated condition. The entire amount of ammonium hydrogen carbonate was 40-50 g. The reaction was monitored using thin layer chromatography [Rf value=0.40, developing solvent: ethyl acetate/acetic acid/methanol/water (volume ratio 4/3/3/1)].

A post treatment designed to remove unreacted ammonium hydrogen carbonate from the reaction system was conducted by cooling the reaction system and allowing ammonium hydrogen carbonate crystals to separate out. In addition to this method, unreacted ammonium hydrogen carbonate may be removed by adding an appropriate amount of water to the reaction system and concentrating the system to vaporize the ammonium hydrogen carbonate or by using a desalination device to remove unreacted ammonium hydrogen carbonate. β-D-glucopyranosylamine was obtained in the manner described.

EXAMPLE 1

A solution of 11-cis-octadecenoic acid obtained by dissolving 282 mg (1.0 millimole, manufactured by the WAKO Co.) in 1 ml of dimethyl sulfoxide was placed in a flask and was used as the reaction system. A solution obtained by dissolving HOBt (153 mg, 1.0 millimole, manufactured by the WAKO Co.) and BOP (1.33 g, 3.0 millimoles, manufactured by the WAKO Co.) in 1.5 ml of dimethyl sulfoxide was added to the reaction system, and the system was agitated using a magnetic stirrer for ten minutes at 25° C.

Next, the β-D-glucopyranosylamine (1.24 g, 6.9 millimoles) obtained in Synthetic Example 1 was added to the reaction system, and the system was agitated using a magnetic stirrer for at least five hours at 25° C. to allow a reaction to occur. This reaction was monitored using thin layer chromatography [Rf value=0.56, developing solvent: chloroform/methanol (volume ratio 4/1)].

The crude product obtained was processed using silica gel column chromatography with a chloroform/methanol mixed solvent (volume ratio 4/1) followed by column chromatography using Toyo Pearl HW-40S (manufactured by the Tosoh Co.) gel permeation agent and methanol as the elution solution to obtain white solids of N-(11-cis-octadecenoyl)-β-D-glucopyranosylamine (85 mg, 19% yield).

The physical properties of this product are described below.

Melting point: 148° C. Elemental analysis ($C_{24}H_{45}O_6N$)

|  | C | H | N |
|---|---|---|---|
| Calculated (%) | 64.98 | 10.22 | 3.16 |
| Experimental (%) | 63.68 | 10.22 | 3.16 |

Figure 2:
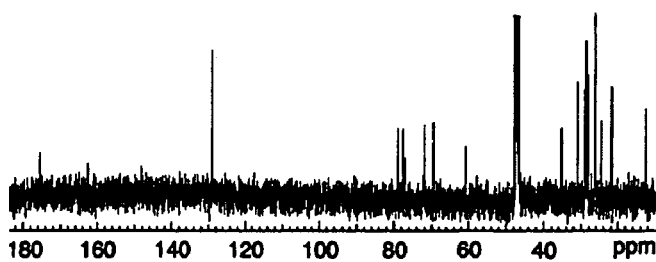
FIG. 2 shows a $^{13}$C-NMR spectrum of the N-glycoside type glycolipid [N-(11-cis-octadecenoyl)-β-D-glucopyranosylamine] prepared in Example 1.

In addition, the $^1$H-NMR spectrum (25° C. in deuterated dimethyl sulfoxide) and the $^{13}$C-NMR spectrum (25° C. in deuterated methanol) of this product are shown in FIGS. 1 and 2, respectively.

In the $^1$H-NMR spectrum (FIG. 1), the δ values were 0.85 ppm (methyl group hydrogens of the hydrocarbon group), 1.24 ppm (methylene group hydrogens of the hydrocarbon group), 1.47 ppm (the hydrogens of the second methylene group of the hydrocarbon groups counted from the amide linkage section), 1.98 ppm (the hydrogens in the first methylene group counted from the vinyl group section of the hydrocarbon group), 2.08 ppm (the hydrogens of the first methylene group counted from the amide linkage of the hydrocarbon group), 3.00-3.65 ppm (the hydrogens connected to the C2, C3, C4, C5 and C6 carbon atoms in the saccharide chain), 4.43-4.94 ppm (the hydroxyl groups connected to the C2, C3, C4, and C6 carbon atoms in the saccharide chain), 4.69 ppm (the hydrogen connected to the C1 carbon in the saccharide chain, dd, J 1,2 9.2 Hz), 5.33 ppm (the hydrogen connected to the vinyl group) and 8.22 ppm (the hydrogen connected to the amide group nitrogen, d, J1, NH 9.2 Hz).

In the $^{13}$C-NMR spectrum (FIG. 2), the δ values were 12.54-35.27 ppm (the carbons in the hydrocarbon groups), 60.76 ppm (the C6 carbon in the saccharide chain), 69.49, 72.02, 77.11 and 77.69 ppm (the C2, C3, C4 and C5 carbons in the saccharide chain), 79.10 ppm (the C1 carbon in the saccharide chain), 128.94 ppm (the carbon in the vinyl group) and 175.51 ppm (the carbon in the amide group).

The analysis results for the N-glycoside type glycolipid obtained from this example agreed with the structural formula (1) and the calculated values were within the error range.

Next, 1 mg of the N-(11-cis-octadecenoyl)-β-D-glucopyranosylamine obtained as described above was weighed into a flask, 20 ml of water was added, and the contents were heated using an oil bath and refluxed for 30 minutes at 95° C. to disperse the solids before the contents were subsequently allowed to stand undisturbed for a little over ten hours.

Figure 3:
FIG. 3 shows a transmission electron microscope (TEM) photograph of the organic nanotube obtained in Example 1. The size of the photograph is 14.2 μm high×14.7 μm wide.
Figure 4:
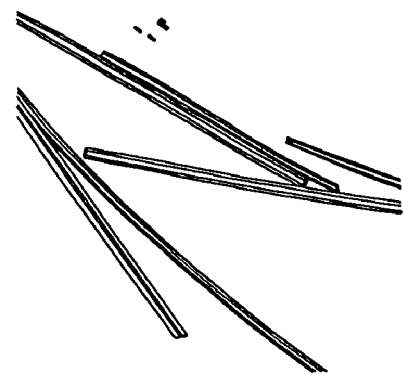
FIG. 4 is a tracing of FIG. 3.
Figure 5:
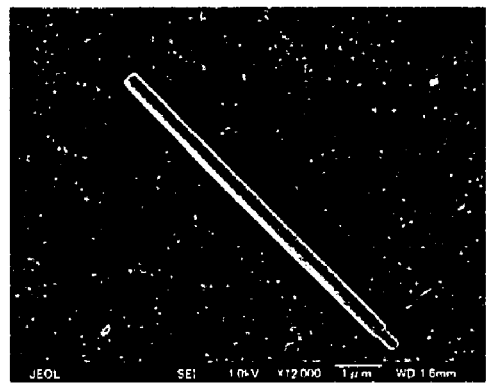
FIG. 5 shows a scanning electron microscope (SEM) photograph of the organic nanotube obtained in Example 1. The size of the photograph is 7.5 μm high×10 μm wide.
Figure 6:
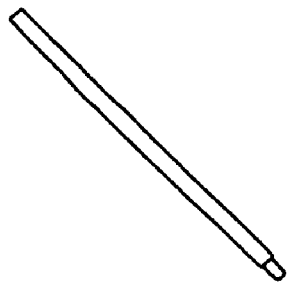
FIG. 6 is a tracing of FIG. 5.
Figure 7:
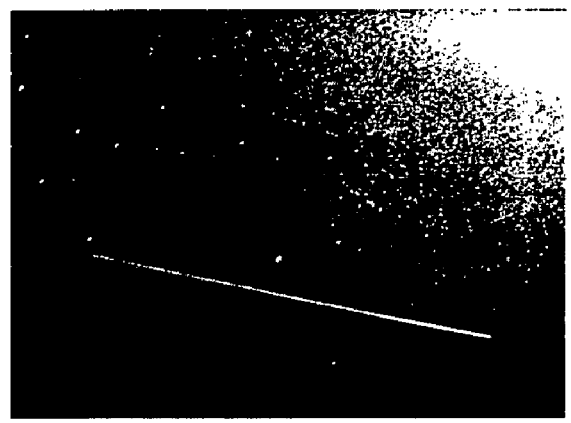
FIG. 7 shows an optical microscope photograph of the organic nanotube obtained in Example 1. The size of the photograph is 0.37 mm high×0.49 mm wide.
Figure 8:
FIG. 8 is a tracing of FIG. 7.

The aqueous solution obtained was examined using a transmission electron microscope, and a hollow fiber type organic nanotube material having an inner diameter of from 45 nm to 200 nm and an external diameter of from 75 nm to 500 nm was confirmed. Furthermore, an examination using an optical microscope confirmed needle like structures from several tens of pm to several hundred pm in length. Transmission electron microscope photographs of these organic nanotubes are shown in FIGS. 3 and 4, scanning electron microscope photographs are shown in FIGS. 5 and 6 and optical microscope photographs are shown in FIGS. 7 and 8.

EXAMPLE 2

The β-D-glucopyranosylamine (40 mg, 0.22 millimole) obtained in Synthetic Example 1 was placed in a flask and was dissolved in 10 ml of methanol to create a reaction system. Triethylamine (154 µl, 1.10 millimole) was added to the reaction system, and the system was immersed in a 0° C. ice bath. Oleoyl chloride (514 µl, 1.32 millimoles, manufactured by the Aldrich Co.) was added in two portions, and the system was agitated using a magnetic stirrer for 19 hours. The reaction was monitored using thin layer 5 chromatography [Rf value=0.47, developing solvent: chloroform/methanol (volume ratio 4/1)].

The crude product obtained was treated using silica gel chromatography with a chloroform/methanol mixed solvent (volume ratio 4/1) as the elution solution, and white solids of N-(9-cis-octadecenoyl)-β-D-glucopyranosylamine (24 mg, 25% yield) were obtained.

The physical properties of this product are described below.

Melting point: 149° C. Elemental analysis ($C_{24}H_{45}O_6N$)

|  | C | H | N |
|---|---|---|---|
| Calculated (%) | 64.98 | 10.22 | 3.16 |
| Experimental (%) | 63.05 | 9.85 | 2.93 |

Next, 1 mg of the N-(9-cis-octadecenoyl)-β-D-glucopyranosylamine obtained as described above was weighed into a flask, 15 ml of water was added, the contents were heated using an oil bath and were refluxed for 30 minutes at 95° C. to disperse the solids before the contents were subsequently allowed to stand undisturbed for about 62 hours.

The aqueous solution obtained was examined using a transmission electron microscope, and a hollow fiber type organic nanotube material having an inner diameter of 20 from 60 nm to 200 nm and an external diameter of from 100 nm to 400 nm was confirmed. (The results are omitted.) Furthermore, an examination using an optical microscope confirmed a needle like structure from several µm to several tens of µm in length.

EXAMPLE 3

9-cis, 12-cis-Octadecadienoic acid (280 mg, 1.0 millimole, manufactured by the Sigma Co.) was weighed into a flask and was dissolved in 1 ml of dimethyl sulfoxide to create a reaction system. HOBt (153 mg, 1.0 millimole) and BOP (537 mg, 3.0 millimoles) were dissolved in 1.5 ml of dimethyl sulfoxide, and the solution was added to the reaction system. The reaction system was agitated using a magnetic stirrer for ten minutes at 25° C.

Next, the β-D-glucopyranosylamine (537 mg, 3.0 millimoles) obtained in Synthetic Example 1 was added to the reaction system and the system was agitated using a magnetic stirrer for at least 5 hours at 25° C. The crude product obtained was processed using silica gel column chromatography using a chloroform/methanol (volume ratio 4/1) mixed solvent as the elution solution. Next, column chromatography was conducted using gel permeation agent Toyo Pearl HW-40S with methanol as the elution solution, and N-(9-cis, 12-cis-octadecadienoyl)-β-D-glucopyranosylamine was obtained.

Next, the N-(9-cis, 12-cis-octadecadienoyl)-β-D-glucopyranosylamine obtained as described above was weighed into a flask, water was added, and the contents were heated using an oil bath and refluxed for 30 minutes at 95° C. to disperse the solids before the contents were subsequently allowed to stand undisturbed for a little over ten hours.

The aqueous solution (or dispersion) obtained was examined using a transmission electron microscope, and a hollow fiber type organic nanotube material was obtained as a precipitate. (The results are omitted.)

EXAMPLE 4

11-cis, 14-cis-Octadecadienoic acid (308 mg, 1.0 millimole, manufactured by the Sigma Co.) was weighed into a flask and was dissolved in 1 ml of dimethyl sulfoxide to create a reaction system. HOBt (153 mg, 1.0 millimole) and BOP (537 mg, 3.0 millimoles) were dissolved in 1.5 ml of dimethyl sulfoxide, and the solution was added to the reaction system. The reaction system was agitated using a magnetic stirrer for ten minutes at 25° C.

Next, the β-D-glucopyranosylamine (537 mg, 3.0 millimoles) obtained in Synthetic Example 1 was added to the reaction system and the system was agitated using a magnetic stirrer for at least 5 hours at 25° C. The crude product obtained was processed using silica gel column chromatography using a chloroform/methanol (volume ratio 4/1) mixed solvent as the elution solution. Next, column chromatography was conducted using gel permeation agent Toyo Pearl HW-40S with methanol as the elution solution, and N-(11-cis, 14-cis-octadecadienoyl)-β-D-glucopyranosylamine was obtained.

Next, the N-(11-cis, 14-cis-octadecadienoyl)-β-D-glucopyranosylamine obtained as described above was weighed into a flask, water was added, and the contents were heated using an oil bath and refluxed for 30 minutes at 95° C. to disperse the solids before the contents were subsequently allowed to stand undisturbed for a little over ten hours.

The aqueous solution obtained was examined using a transmission electron microscope, and a hollow fiber type organic nanotube material was obtained as a precipitate. (The results are omitted.)

EXAMPLE 5

11-cis, 14-cis, 17-cis-Eicosatrienoic acid (306 mg, 1.0 millimole, manufactured by the Sigma Co.) was weighed into a flask and was dissolved in 1 ml of dimethyl sulfoxide to create a reaction system. HOBt (153 mg, 1.0 millimole) and BOP (537 mg, 3.0 millimoles) were dissolved in 1.5 ml of dimethyl sulfoxide, and the solution was added to the reaction system. The reaction system was agitated using a magnetic stirrer for ten minutes at 25° C.

Next, the β-D-glucopyranosylamine (537 mg, 3.0 millimoles) obtained in Synthetic Example 1 was added to the reaction system and the system was agitated using a magnetic stirrer for at least 5 hours at 25° C. The crude product obtained was processed using silica gel column chromatography using a chloroform/methanol (volume ratio 4/1) mixed solvent as the elution solution. Next, column chromatography was conducted using gel permeation agent Toyo Pearl HW-40S with methanol as the elution solution, and N-(11-cis, 14-cis, 17-cis-eicosatrienoyl)-β-D-glucopyranosylamine was obtained.

Next, the N-(11-cis, 14-cis-octadecadienoyl)-β-D-glucopyranosylamine obtained as described above was weighed into a flask, water was added, and the contents were heated using an oil bath and refluxed for 30 minutes at 95° C. to disperse the solids before the contents were subsequently allowed to stand undisturbed for a little over ten hours.

The aqueous solution ["dispersion", "mixture" or "suspension"] obtained was examined using a transmission electron microscope, and a hollow fiber type organic nanotube material was obtained as a precipitate. (The results are omitted.)

COMPARATIVE EXAMPLE 1

The β-D-glucopyranosylamine (358 mg, 20 millimole) obtained in Synthetic Example 1 was placed in a flask and was dissolved in 80 ml of methanol and 50 ml of tetrahydrofuran. Triethylamine (1.39 ml, 10 millimole) was added to the reaction mixture, and the mixture was immersed in an ice bath at 0° C. Stearoyl chloride (4.84 g, 16 millimoles) was added in four portions, and the mixture was agitated using a magnetic stirrer for 43 hours. The reaction was monitored using thin layer chromatography [Rf value=0.55, developing solvent: chloroform/methanol (volume ratio 4/1)]. The crude product obtained was processed using silica gel chromatography with a chloroform/methanol mixed solvent (volume ratio 4/1) as the elution solution, and white solids of N-octadecanoyl-β-D-glucopyranosylamine (26 mg, 3% yield) were obtained.

One milligram of the N-octadecanoyl-β-D-glucopyranosylamine obtained was weighed into a flask, 30 ml of water was added, the system was heated using an oil bath and refluxed for 30 minutes at 95° C. However, only a portion of the sample was dispersed. The system was allowed to stand undisturbed at room temperature for about eight days. The aqueous solution ['dispersion," "mixture" or "suspension"] containing a fiber shaped material obtained was collected and was examined using a transmission electron microscope. The majority of the material was present as spherical masses but some hollow fiber shaped organic nanotubes having an external diameter of from 120 nm to 300 nm were confirmed.

The invention claimed is:

1. A hollow fiber shaped organic nanotube having an average external diameter of the nanotubes of 70 nm to 500 nm and an average internal diameter of 40 nm to 300 nm comprising an N-glycoside glycolipid as the constitutional component represented by the general formula (1)

G-NHCO—R         (1)

wherein, G represents a sacoharide selected from the group consisting of glucopyranose, galactopyranose, maltose, lactose, and cellobiose radical from which the hemiacetal hydroxyl group bonded to the anomer carbon atom of the saccharide is excluded, and R represents a linear unsaturated hydrocarbon group containing 10-39 carbon atoms.

2. A hollow fiber shaped organic nanotube as in claim 1 wherein the saccharide is a monosaccharide.

3. A hollow fiber shaped organic nanotube having an average external diameter of the nanotubes of 70 nm to 500 nm and an average internal diameter of 40 nm to 300 nm comprising an N-glycoside glycolipid as the constitutional component represented by the general formula (1)

G-NHCO—R         (1)

wherein, G represents a glucose radical from which the hemiacetal hydroxyl group bonded to the anomer carbon of the saccharide is excluded, and R represents a linear unsaturated hydrocarbon group containing 10-39 carbon atoms.

* * * * *